United States Patent [19]

Cattani

[11] Patent Number: 4,824,083
[45] Date of Patent: Apr. 25, 1989

[54] WORK REST, AS USED IN PARTICULAR BY DENTAL TECHNICIANS AND GOLDSMITHS

[75] Inventor: Augusto Cattani, Parma, Italy

[73] Assignees: Officine Augusto Cattani & C. S.P.A., Italy; Daicel Chemical Industries Ltd., Japan

[21] Appl. No.: 136,291

[22] Filed: Dec. 22, 1987

[30] Foreign Application Priority Data

Jan. 30, 1987 [IT] Italy ................................ 2890487[U]

[51] Int. Cl.⁴ .............................................. B23Q 3/00
[52] U.S. Cl. .................................................... 269/15
[58] Field of Search .............. 72/39; 409/219; 269/15, 269/327; 98/36, 115.1, 115.2, 115.3; 422/104; 83/100

[56] References Cited

U.S. PATENT DOCUMENTS

| 4,300,421 | 11/1981 | Yano et al. | 83/100 |
| 4,576,072 | 3/1986 | Terpstra et al. | 83/100 |
| 4,650,171 | 3/1987 | Howorth | 269/327 |

FOREIGN PATENT DOCUMENTS

| 2711435 | 9/1978 | Fed. Rep. of Germany | 269/15 |
| 653995 | 5/1951 | United Kingdom | 269/15 |

Primary Examiner—Robert C. Watson
Attorney, Agent, or Firm—Darby & Darby

[57] ABSTRACT

The work rest is typical of those used by dental technicians and goldsmiths, but comprises an air intake point (7) at the side of the work area (4) remote from the craftsman; this connects directly with a suction pipe (5) beneath and is surmounted by a folding cowl (9) consisting in a rear member (10), rigidly interconnecting two side members (11), and a top member (13) hinged between centers near the top edge of the rear member. The entire cowl assembly pivots about a horizontal axis adjacent to the rear edge of the air intake (7).

7 Claims, 2 Drawing Sheets

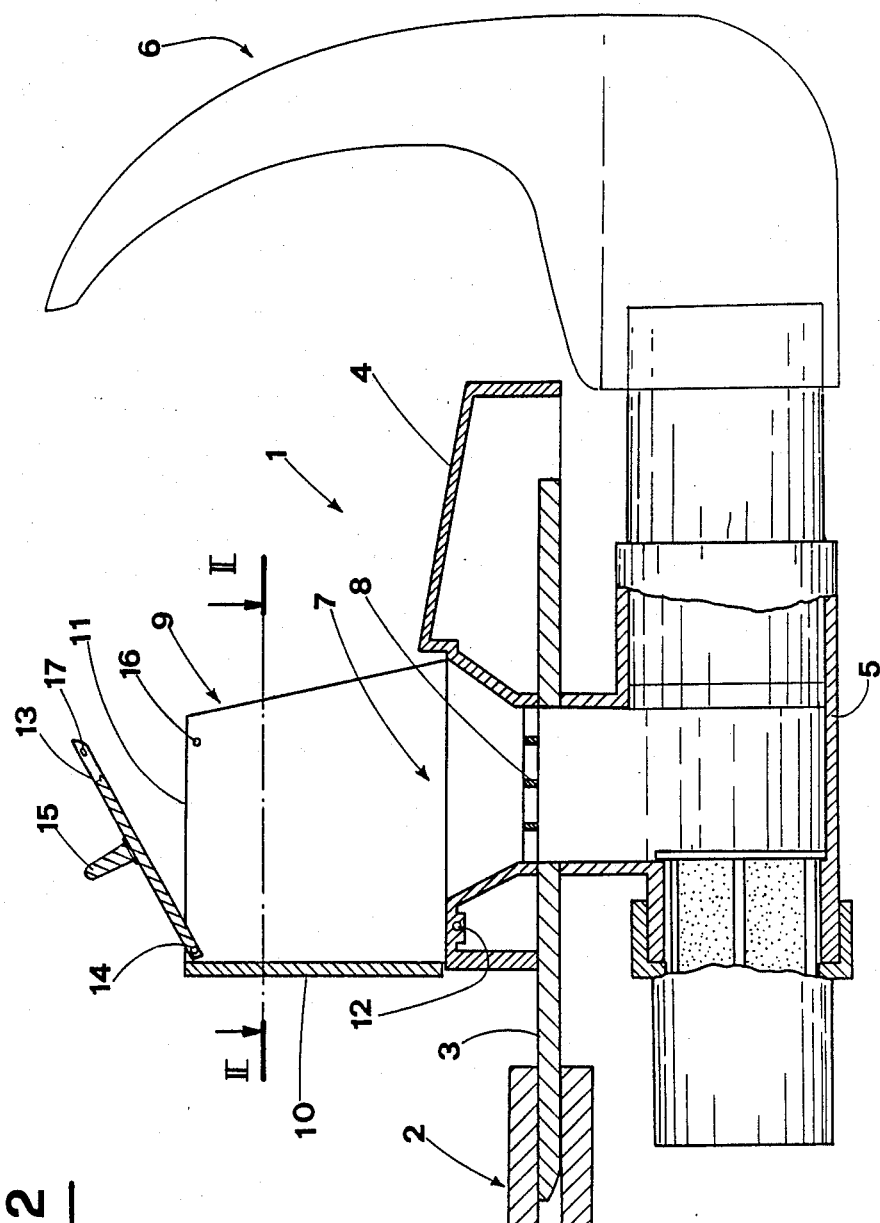

WORK REST, AS USED IN PARTICULAR BY DENTAL TECHNICIANS AND GOLDSMITHS

BACKGROUND OF THE INVENTION

The invention relates to a work rest, as used in particular by dental technicians and goldsmiths, and is intended specifically, though not exclusively, for those work rest assemblies that are attached to a bench and coupled to an air extraction system which facilitates the recovery of precious metals, or the removal of dust that may constitute a hazard to the respiratory system.

Such work rests comprise a stock that is fitted to the bench, and serves to carry an assembly including the work rest proper, located uppermost, and beneath the rest, a length of pipe arranged such that an extractor port, fashioned from transparent material in the general semblance of a shield, or shell, can be fitted to its front end, between the work rest and the craftsman.

Suction generated near the work area must respond to precise requirements: on the one hand, the draft created must not be too fierce; on the other hand, the dust produced at the work area must be removed efficiently and completely. More exactly, the dust projected by the tool should be picked up at a short distance from the work, using a gentle draft, and to this end, a shield made of a transparent material is attached to the front end of the work rest. Dust is removed from behind and above the work area using movable ports that are attached to flexible suction ducts and carried on brackets that can be arranged for position, by the craftsman, to best advantage.

The object of the invention disclosed is to ensure efficient dust extraction from behind the work area of rests used by dental technicians or goldsmiths, adopting a particularly simple expedient and utilizing the same suction duct as that to which the transparent front extractor port is connected.

A further object of the invention is to embody a rear dust extraction facility that is capable of meeting the widest possible range of requirements, and in particular, that of being dispensed with when not needed for the job in hand, without in any way causing an obstruction around the work area.

One of the advantages provided by the invention is its simplicity in terms of construction.

SUMMARY OF THE INVENTION

The stated objects and others are realized with the invention, which relates to a work rest, as used in particular by dental technicians and goldsmiths, of the type comprising a stock that is fitted to the craftman's work bench and carries a structure that incorporates the work rest proper, uppermost, and beneath the rest, a length of suction pipe arranged in such a way that a transparent extractor port can be fitted to its front end, between the work rest and the craftsman.

According to the invention, an air intake is located to the rear of the work rest, remote from the craftsman, and connected directly to the suction pipe beneath, through which a downward air draft is created, and surmounted by a folding cowl consisting in a plurality of movable members that include a rear member, rigidly interconnecting two parallel side members that are hinged at the bottom and rotatable about an axis adjacent to the rear edge of the air intake; thus, the cowl rotates between a folded-down position, in which the rear member is horizontal, blocking the air intake, and a fully open position in which the rear member is upright.

BRIEF DESCRIPTION OF THE DRAWINGS

The invention will now be described in detail, by way of example, with the aid of the accompanying drawings, in which:

FIG. 2 is the section through I—I in FIG. 1;

DESCRIPTION OF THE PREFERRED EMBODIMENT

Figure 3:
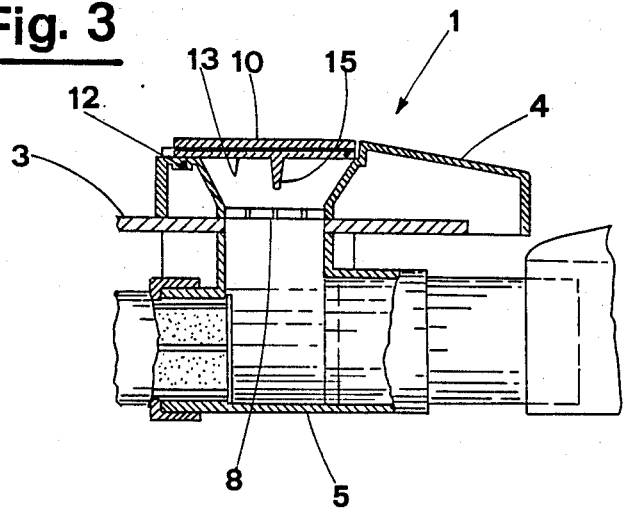
FIG. 3 illustrates the work rest in the same section as that of FIG. 2, but seen in a different operating configuration.

With reference to the drawings, 1 denotes a work rest, in its entirety, as designed specifically for dental technicians and goldsmiths.

Such work rests comprise a stock 2, which is stably bolted or screwed to the craftsman's work bench and affords a slot in which to insert a plate, or tang 3 that forms part of an assembly comprising the work area proper, denoted 4 and located uppermost, and beneath, a length of pipe 5 through which suction is generated.

6 denotes a transparent shield or shell which is attached to the front, projecting end of the pipe 5, between the craftsman and the work area 4. In the event of it being wished to recover the waste removed from the material being worked, e.g. gold or other precious metals, a filter will be installed internally of the pipe 5, to as to trap particles entrained by the dust-laden air drawn in from the various extractor ports.

The area to the rear of the work area 4, i.e. remote from the craftsman, is also provided with an air intake 7 disposed substantially in a horizontal position, or at all events, such that suction draws air downwards and directly into the pipe 5 below. The air intake 7 is furnished with a grille 8, and is provided above with a folding cowl 9 formed from mutually hinged members.

More exactly, the cowl 9 comprises a substantially flat rear member 10 rigidly attached at right angles to two identical parallel side members 11 which are rotatably attached at bottom, by way of a horizontal pivot 12, to the rear part of the air intake 7 (remote from the craftsman); thus, when folded down, (FIG. 3), the rear member 10 will lie substantially horizontal, covering the air intake 7. The pivot 12 is positioned in such a way that with the cowl fully opened up, the rear member 10 will be substantially upright (FIG. 2).

It will be observed that the position of the cowl 9 is infinitely variable between the fully open and folded-down positions.

In addition to the rear and side members 10 and 11, the folding cowl 9 further comprises a movable top member, denoted 13, carried by a pivot 14 the axis of which lies adjacent to the top edge of the rear member 10 and parallel both to the top edge itself and to the axis of the lower pivot 12. This movable member 13 is disposed normal to the parallel side members 11, filling the space between them in such a way as to constitute a lid when the rear member 10 is in the upright position, i.e. when the cowl 9 is fully opened up.

The top member 13 is thus hinged to the two parallel side members 11 by way of the pivot 14, and can be rotated freely about the axis of the pivot to assume any given angular position within an arc of at least 180°, departing from the folded down position shown in FIG. 3, in which it is breasted flat against the inside face of the rear member 10, transverse to the air intake 7.

15 denotes a member issuing from the outside surface of the top member 113, serving as a handle by means of which to sieze the top member and rotate it into the desired position. The hinged top member 13 is set and held in position in relation to the side members 11 by means of stops 16, appearing in FIG. 2 as projecting elements located on the inside faces of the side members themselves, that function as plungers by inserting into recesses 17 located in the edges of the top member 13.

The manner in which the invention operates will be clear enough to discern.

Figure 1:
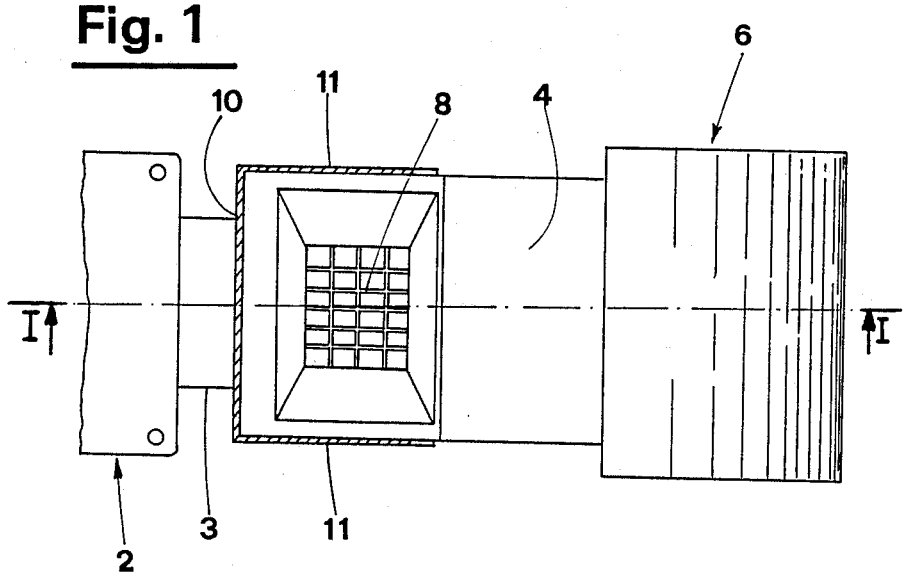
FIG. 1 is a schematic representation of the work rest viewed in plan, and partly in section taken through II—II in FIG. 2.

In the configuration of FIG. 1, with the rear member 10 upright, a gentle air current is created at the back of the work area 4, that is, a suction draft which is weak in terms of velocity, but which operates in close proximity to the work area and is therefore able to draw in dust from the work with significant ease. With the top member 13 tiltable back and forwards, the top of the cowl 9 can either be covered or left open, and the craftsman has an additional facility for adjustment of the draft, by varying the contour and the cross section of the cowl 9 as a whole.

In the event that no draft is required behind the work area 4, the cowl can be made to disappear, for all practical intents and purposes, by tucking the top member 13 away against the rear member 10 and then rotating the rear and side members about their pivot 12 through 90° approx in such a way that the air intake 7 is blanked off completely. In this, the folded down position, the work area remains entirely unobstructed.

What is claimed:

1. A work arrangement, comprising
a base having a support structure, a suction pipe located at a distance from said base, an air intake connecting said suction pipe with the base, said air intake having a neck portion situated within said base and in the vicinity of the support structure, a folding cover having at least a part situated within said neck portion and having two side walls and a cross wall interconnecting said side walls, said cross wall being pivotally attached to said neck portion, said cross wall being movable between open and closed positions,
wherein in the closed position said cross wall closes said neck portion of the air intake, and in the open position said cross wall supports said side walls in an upright position so that a box-type structure open toward the support structure is defined.

2. A work arrangement according to claim 1 wherein said cross wall having at least two ends, a first end being pivotally attached to the neck portion and a second end being free, a movable top member being pivotally attached to said free end of the cross wall, a pivotal axis of said movable top member being substantially parallel to a pivotal axis of the cross wall when it pivots about said neck portion, said movable member being movable about its pivotal axis between folded and unfolded positions within an arc of at least 180°,
wherein in said folded position said movable member closely engages with said cross wall.

3. A work arrangement according to claim 2 wherein said cross wall and said movable member each having a working surface, and in the folded position said working surfaces of the cross wall and the movable member closely engage each other.

4. A work arrangement according to claim 3 wherein a handling member extends outwardly from said movable member to facilitate handling and rotation of said movable member.

5. A work arrangement according to claim 4 wherein said handling member extends from a surface of said movable member opposite to said working surface.

6. A work arrangement according to claim 2 wherein a stop element protrudes from at least one said side walls, said stop element is adapted to hold said movable member in predetermined position within said box-type structure.

7. A work arrangement according to claim 1 wherein said suction pipe is positioned substantially below said base.

* * * * *